US012620479B2

(12) United States Patent
Hayashitani et al.

(10) Patent No.: US 12,620,479 B2
(45) Date of Patent: May 5, 2026

(54) INFORMATION PROCESSING DEVICE, INFORMATION PROCESSING METHOD, AND RECORDING MEDIUM

(71) Applicant: NEC Corporation, Tokyo (JP)

(72) Inventors: Masahiro Hayashitani, Tokyo (JP); Eiji Yumoto, Tokyo (JP); Takeshi Hasegawa, Tokyo (JP); Yuki Kosaka, Tokyo (JP); Kosuke Nishihara, Tokyo (JP); Yutaka Uno, Tokyo (JP); Yuan Luo, Tokyo (JP); Kenji Araki, Tokyo (JP); Makoto Yasukawa, Tokyo (JP); Shuhei Noyori, Tokyo (JP); Yusuke Ito, Tokyo (JP)

(73) Assignee: NEC CORPORATION, Tokyo (JP)

( * ) Notice: Subject to any disclaimer, the term of this patent is extended or adjusted under 35 U.S.C. 154(b) by 195 days.

(21) Appl. No.: 18/227,242

(22) Filed: Jul. 27, 2023

(65) Prior Publication Data

US 2024/0038372 A1     Feb. 1, 2024

(30) Foreign Application Priority Data

Jul. 29, 2022     (JP) ................................ 2022-121637

(51) Int. Cl.
*G16H 40/20*          (2018.01)
*G16H 10/60*          (2018.01)
(52) U.S. Cl.
CPC ............. *G16H 40/20* (2018.01); *G16H 10/60* (2018.01)

(58) Field of Classification Search
CPC ............................... G16H 40/20; G16H 10/60
See application file for complete search history.

(56) References Cited

U.S. PATENT DOCUMENTS

2015/0213224 A1*   7/2015   Amarasingham ...... G16H 50/30
                                                                    705/2
2015/0371350 A1   12/2015   Zebarjadi et al.
2020/0243196 A1    7/2020   Ohno et al.

FOREIGN PATENT DOCUMENTS

CA          2861824 C   *   3/2020   ............. G06Q 10/00
JP      2013-152632 A       8/2013
WO      2019/073927 A1      4/2019

OTHER PUBLICATIONS

Author(s): Rahimi Title: New dynamic integrated frame work for surgical patients prioritization Journal: Elsevier [online]. Publication date: 2016 [retrieved on: Jan. 11, 2025 ]. Retrieved from the Internet: < URL: https://www.sciencedirect.com/science/article/pii/S0167923616300860> (Year: 2016).*
JP Office Action for JP Application No. 2022-121637, mailed on Mar. 3, 2026 with English Translation.

* cited by examiner

*Primary Examiner* — Aryan E Weisenfeld
(74) *Attorney, Agent, or Firm* — Sughrue Mion, PLLC

(57)          ABSTRACT
In information processing device, the information acquisition means acquires patient information, medical professional information, and environment information. The treatment order determination means determines an order of treatment of the patients for each medical professional based on the patient information, the medical professional information, and the environment information.

13 Claims, 12 Drawing Sheets

| PATIENT NAME | BASIC INFORMATION OF THE PATIENT | | BIOMEDICAL INFORMATION (HEART RATE) | DISQUIET SCORE | BEHAVIOR |
|---|---|---|---|---|---|
| | SEX | AGE | | | |
| A | MALE | 80 | 110bpm | 0.8 | MOVEMENT |
| B | MALE | 60 | 70bpm | 0.0 | NO MOVEMENT |
| C | XX | XX | XX | XX | XX |
| D | XX | XX | XX | XX | XX |
| . | . | . | . | . | . |
| Z | XX | XX | XX | XX | XX |

| MEDICAL PROFESSIONAL NAME | LENGTH OF SERVICE | SKILL LEVEL | PATIENTS IN CHARGE |
|---|---|---|---|
| S | 10 YEARS | 4 | A、B、C、・・・ |
| T | 5 YEARS | 3 | D、E、・・・ |

| PATIENT NAME | PATIENT'S ROOM INFORMATION | ACCESS INFORMATION | |
|---|---|---|---|
| | | DISTANCE FROM S | DISTANCE FROM T |
| A | ICU | ●●m | ●●m |
| B | GENERAL WARD | △△m | △△m |
| C | XX | XX | XX |
| D | XX | XX | XX |
| . | . | . | . |
| Z | XX | XX | XX |

FIG. 8

| PATIENT NAME | TOTAL COST | |
|---|---|---|
| | S | T |
| A | 14 | 10 |
| B | 0 | 0 |
| C | 15 | 11 |
| D | 3 | 5 |
| E | 12 | 15 |
| . | . | . |
| Z | 5 | 4 |

INFORMATION OF
PATIENTS TO TREAT

USER NAME : S

| PATIENT | COST | TREATMENT ORDER |
|---------|------|-----------------|
| A | 14 | 2 |
| C | 15 | 1 |
| E | 12 | T will treat |
| F | 11 | T will treat |

INFORMATION OF
PATIENTS TO TREAT

USER NAME : T

| PATIENT | COST | TREATMENT ORDER |
|---------|------|-----------------|
| A | 10 | S will treat |
| C | 11 | S will treat |
| E | 15 | 1 |
| F | 14 | 2 |

INFORMATION OF PATIENTS TO TREAT

ADMINISTRATOR : U

| PATIENT | COST | | MEDICAL PROFESSIONAL TO TREAT | TREATMENT ORDER |
|---|---|---|---|---|
| | NURSE S | NURSE T | | |
| A | 14 | 10 | S | 2 |
| B | 15 | 11 | S | 1 |
| C | 12 | 15 | T | 1 |
| D | 11 | 14 | T | 2 |

FIG. 11

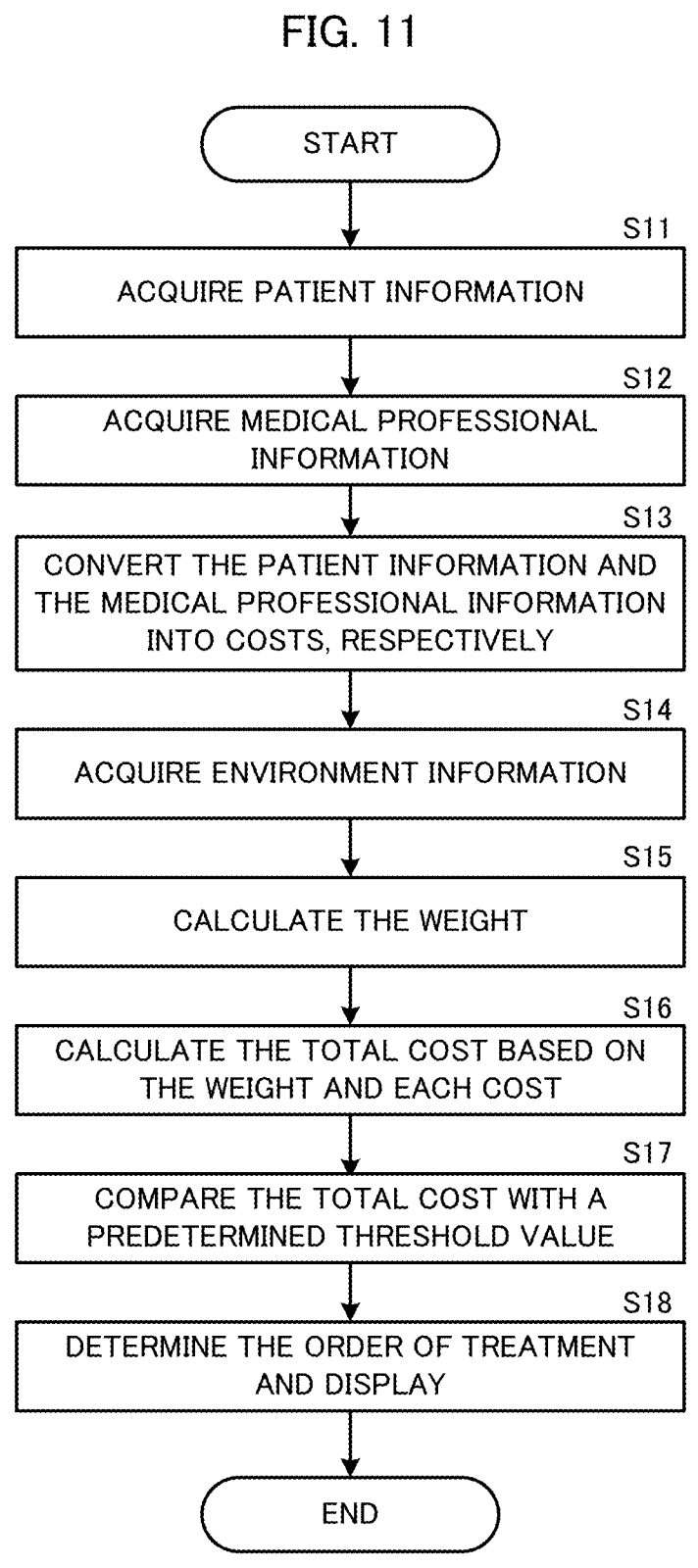

```
                    ┌──────────────┐
                    │    START     │
                    └──────┬───────┘
                           │              S11
           ┌───────────────▼───────────────┐
           │   ACQUIRE PATIENT INFORMATION  │
           └───────────────┬───────────────┘
                           │              S12
           ┌───────────────▼───────────────┐
           │   ACQUIRE MEDICAL PROFESSIONAL │
           │          INFORMATION           │
           └───────────────┬───────────────┘
                           │              S13
           ┌───────────────▼───────────────┐
           │ CONVERT THE PATIENT INFORMATION AND │
           │ THE MEDICAL PROFESSIONAL INFORMATION │
           │     INTO COSTS, RESPECTIVELY    │
           └───────────────┬───────────────┘
                           │              S14
           ┌───────────────▼───────────────┐
           │ ACQUIRE ENVIRONMENT INFORMATION │
           └───────────────┬───────────────┘
                           │              S15
           ┌───────────────▼───────────────┐
           │      CALCULATE THE WEIGHT      │
           └───────────────┬───────────────┘
                           │              S16
           ┌───────────────▼───────────────┐
           │ CALCULATE THE TOTAL COST BASED ON │
           │    THE WEIGHT AND EACH COST    │
           └───────────────┬───────────────┘
                           │              S17
           ┌───────────────▼───────────────┐
           │ COMPARE THE TOTAL COST WITH A  │
           │ PREDETERMINED THRESHOLD VALUE  │
           └───────────────┬───────────────┘
                           │              S18
           ┌───────────────▼───────────────┐
           │ DETERMINE THE ORDER OF TREATMENT │
           │          AND DISPLAY           │
           └───────────────┬───────────────┘
                           │
                    ┌──────▼───────┐
                    │     END      │
                    └──────────────┘
```

INFORMATION OF PATIENTS TO TREAT

USER NAME : S

| PATIENT | COST | TREATMENT ORDER | APPROVAL |
|---------|------|-----------------|----------|
| A | 14 | 2 | OK |
| C | 15 | 1 | OK |
| E | 12 | T will treat | OK |
| F | 11 | T will treat | OK |

INFORMATION OF PATIENTS TO TREAT

USER NAME : T

| PATIENT | COST | TREATMENT ORDER | APPROVAL |
|---------|------|-----------------|----------|
| A | 10 | S will treat | OK |
| C | 11 | S will treat | OK |
| E | 15 | 1 | OK |
| F | 14 | 2 | OK |

| INFORMATION OF PATIENTS TO TREAT | | | | | |
|---|---|---|---|---|---|
| ADMINISTRATOR : U | | | | | |
| PATIENT | COST | | MEDICAL PROFESSIONAL TO TREAT | TREATMENT ORDER | APPROVAL |
| | NURSE S | NURSE T | | | |
| A | 14 | 10 | S | 2 | OK  NG |
| B | 15 | 11 | S | 1 | OK  NG |
| C | 12 | 15 | T | 1 | OK  NG |
| D | 11 | 14 | T | 2 | OK  NG |

FIG. 14

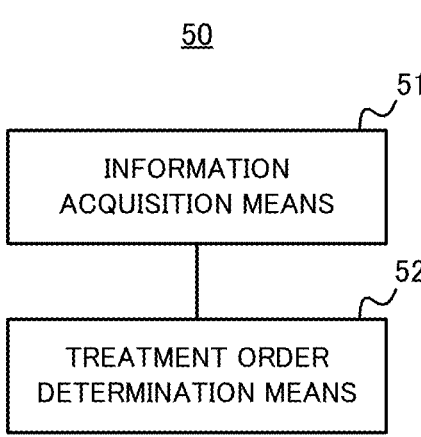

50

```
┌─────────────────────────┐  51
│   INFORMATION           │
│   ACQUISITION MEANS     │
└─────────────────────────┘
            │
┌─────────────────────────┐  52
│   TREATMENT ORDER       │
│   DETERMINATION MEANS   │
└─────────────────────────┘
```

FIG. 15

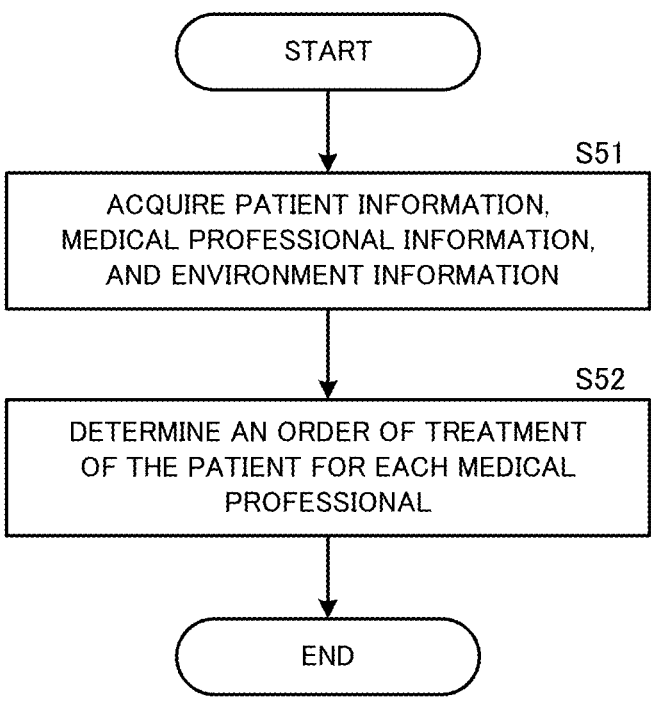

START

S51
ACQUIRE PATIENT INFORMATION,
MEDICAL PROFESSIONAL INFORMATION,
AND ENVIRONMENT INFORMATION

S52
DETERMINE AN ORDER OF TREATMENT
OF THE PATIENT FOR EACH MEDICAL
PROFESSIONAL

END

INFORMATION PROCESSING DEVICE, INFORMATION PROCESSING METHOD, AND RECORDING MEDIUM

TECHNICAL FIELD

The present invention relates to a determination of patient's treatment order.

BACKGROUND ART

In medical facilities such as hospitals, disquiet may occur in patients. Disquiet is the state of confusion associated with the occurrence of delirium or the like that may occur in a patient. Problem behaviors such as self-extubation, over-turning, and falling occur when an inpatient becomes disquiet, which increases the risk of delayed treatment and injury. Patent Document 1 proposes a mechanism for estimating countermeasure information by detecting indications of disquiet in advance.

PRECEDING TECHNICAL REFERENCES

Patent Document

Patent Document 1: International Publication No. WO2019/073927

SUMMARY

Problem to be Solved by the Invention

However, in Patent Document 1, when a plurality of patients becomes disquiet, a patient's treatment order, such as from which patient to treat, has not been considered.

It is an object of the present disclosure to provide an information processing device capable of efficiently treating patients by determining a patient's treatment order.

Means for Solving the Problem

According to an example aspect of the present invention, there is provided an information processing device comprising:

an information acquisition means configured to acquire patient information, medical professional information, and environment information; and a treatment order determination means configured to determine an order of treatment of patients for each medical professional based on the patient information, the medical professional information, and the environment information.

According to another example aspect of the present invention, there is provided an information processing method comprising:

acquiring patient information, medical professional information, and environment information; and determining an order of treatment of the patients for each medical professional based on the patient information, the medical professional information, and the environment information.

According to still another example aspect of the present invention, there is provided a recording medium recording a program which causes a computer to execute processing of:

acquiring patient information, medical professional information, and environment information; and determining an order of treatments of the patient for each medical professional based on the patient information, the medical professional information, and the environment information.

Effect of the Invention

According to the present invention, it is possible to efficiently treat patients by determining a patient's treatment order.

BRIEF DESCRIPTION OF THE DRAWINGS

FIG. 5 is an example of a data structure of a patient information storage unit.

FIG. 6 is an example of a data structure of a medical professional information storage unit.

FIG. 7 is an example of a data structure of an environment information storage unit.

FIG. 8 is an example of a total cost.

FIGS. 9A and 9B are examples of displaying information transmitted by the server.

FIG. 10 is another example of displaying information transmitted by the server.

FIG. 11 is a flowchart of a treatment order determination processing according to the first example embodiment.

FIGS. 12A and 12B are other examples of displaying information transmitted by the server.

FIG. 13 is another example of displaying information transmitted by the server.

FIG. 14 is a block diagram showing a functional configuration of an information processing device according to a second example embodiment.

FIG. 15 is a flowchart of processing in the second example embodiment.

EXAMPLE EMBODIMENTS

First Example Embodiment

[System Configuration]

Figure 1:
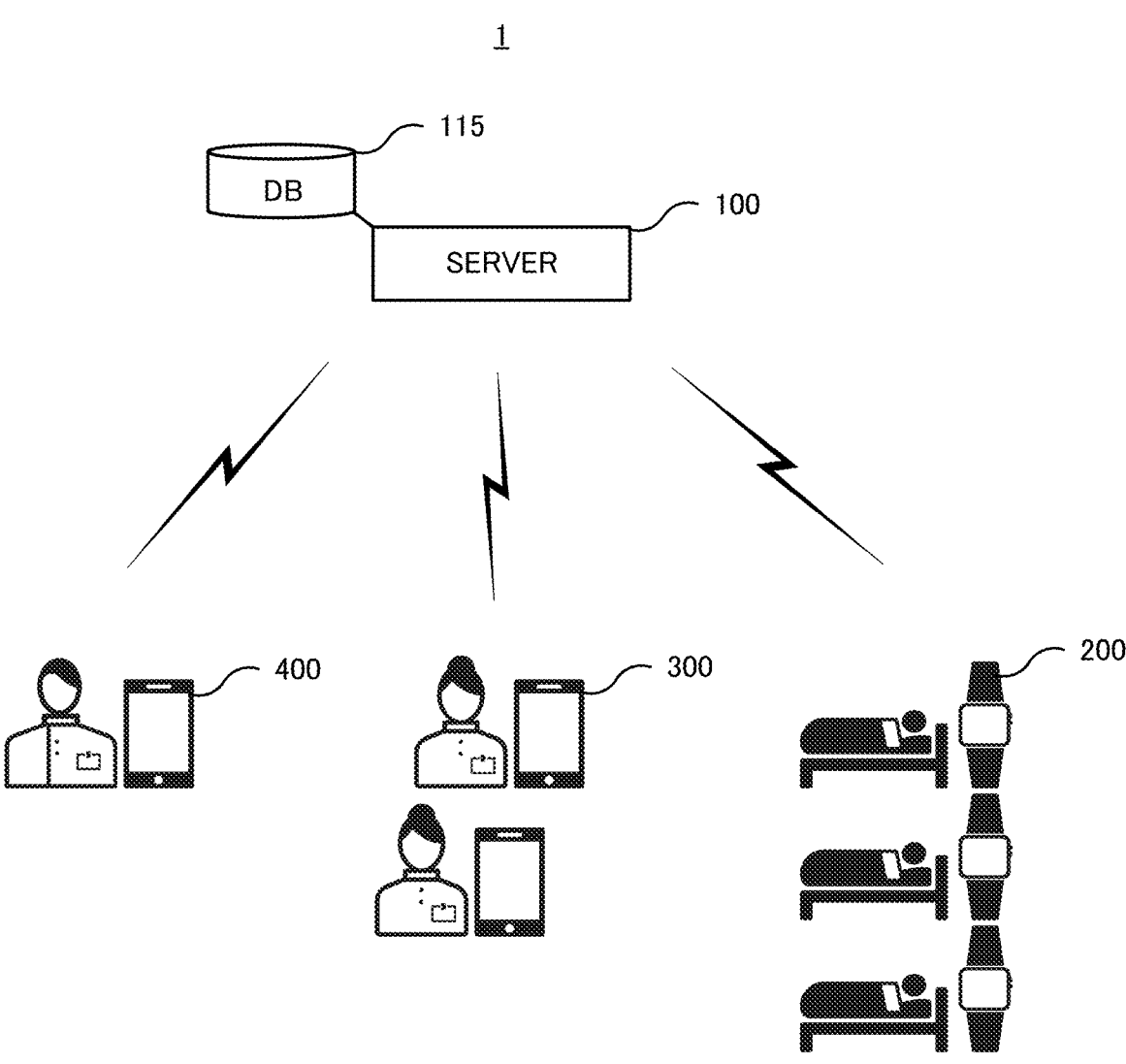
FIG. 1 shows an overall configuration of a patient's treatment order presentation system according to a first example embodiment.

FIG. 1 shows an overall configuration of a patient's treatment order presentation system to which an information processing device according to the present disclosure is applied. The patient's treatment order presentation system 1 includes a server 100, patient terminals 200, medical professional terminals 300, and an administrator terminal 400. The server 100 is connected to a database 115. The server 100 is an example of the information processing device. The server 100 and the patient terminal 200 can communicate wirelessly. The server 100 and the medical professional terminal 300 can communicate wirelessly. The server 100 and the administrator terminal 400 can communicate wirelessly. In addition, it is assumed that there are multiple patient terminals 200 and multiple medical professional terminals 300.

The server 100 determines medical professionals to treat disquiet patients or patients at risk of being disquiet, and the priority of treatment. Specifically, the server 100 acquires information about patients (hereinafter referred to as the "patient information"), information about the medical professionals (hereinafter referred to as the "medical professional information"), and information about environments (hereinafter referred to as the "environment information") from the database 115 at each predetermined time. Then, the server 100 decides patients who need to be treated, the medical professionals who treat, and the priority of treatment based on the patient information, the medical professional information, and the environment information. The server 100 generates display data including the patients who need to be treated, the medical professionals who treat, the priority of treatment, and the like. Then, the server 100 transmits the display data to the medical professional terminals 300 and the administrator terminal 400.

Incidentally, the database 115 stores the patient information, the medical professional information, and the environment information, in advance. The server 100 receives biomedical information and location information from the patient terminals 200 and the medical professional terminals 300, and updates the predetermined information in the database 115 at each predetermined time.

The patient terminal 200 is, for example, a wristband type wearable device. The patient terminal 200 acquires the biomedical information and the location information of a patient at each predetermined time and transmits the information to the server 100. The biomedical information of the patient includes, for example, a heart rate, a respiratory rate, blood pressure, a body temperature, and a perspiration amount. Incidentally, the biomedical information of the patient may be acquired from a thermographic camera or the like installed in the hospital room in advance.

The medical professional terminal 300 is a terminal used by a medical professional such as a nurse, and is a smartphone or a tablet terminal, for example. The medical professional terminal 300 acquires the location information and transmits the location information to the server 100 at each predetermined time. In addition, the medical professional terminal 300 displays the display data received from the server 100 on the display. Thus, the medical professional can understand the patients who they should treat and the order of treatment.

The administrator terminal 400 is a terminal used by an administrator such as a doctor or a nurse chief, and is a smartphone, a tablet terminal or the like. The administrator terminal 400 displays the display data received from the server 100 on the display. Thus, the administrator can understand which medical professional treats which patient.

[Server]

Figure 2:
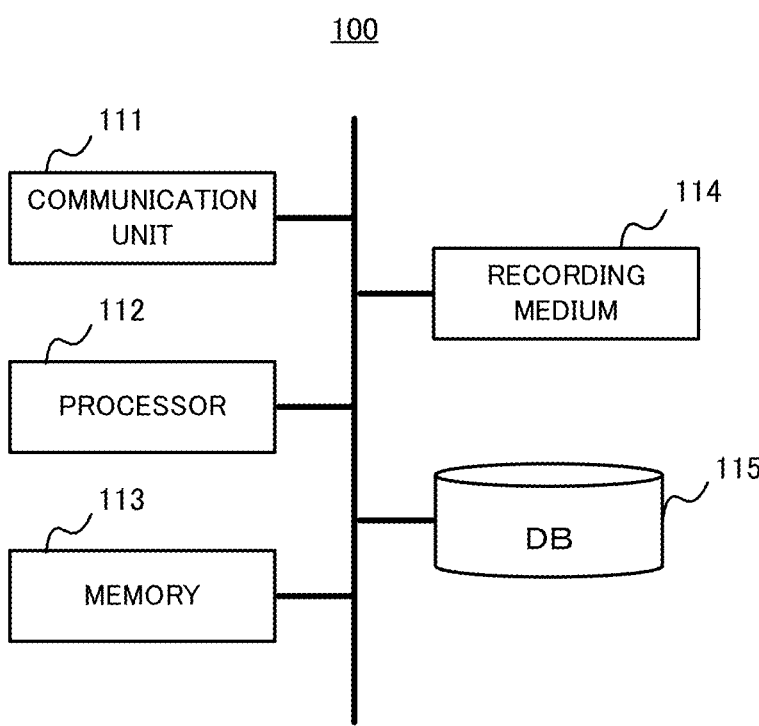
FIG. 2 is a block diagram showing a configuration of a server.

FIG. 2 is a block diagram showing a configuration of the server 100. The server 100 mainly includes a communication unit 111, a processor 112, a memory 113, a recording medium 114, and a data base (DB) 115.

The communication unit 111 transmits and receives data to and from external devices. Specifically, the communication unit 111 transmits and receives information to and from the patient terminals 200, the medical professional terminals 300, and the administrator terminal 400.

The processor 112 is a computer, such as a CPU (Central Processing Unit) and controls the entire server 100 by executing a program prepared in advance. The processor 112 may be a GPU (Graphics Processing Unit), a FPGA (Field- Programmable Gate Array), a DSP (Demand-Side Platform), an ASIC (Application Specific Integrated Circuit), or the like.

The memory 113 may be a ROM (Read Only Memory) and a RAM (Random Access Memory). The memory 113 stores various programs executed by the processor 112. The memory 113 is also used as a working memory during various processes performed by the processor 112.

The recording medium 114 is a non-volatile and non-transitory recording medium such as a disk-like recording medium and a semiconductor memory, and is configured to be detachable from the server 100. The recording medium 114 records various programs executed by the processor 112.

The database (DB) 115 stores the patient information, the medical professional information, the environment information, or the like. The DB 115 may include an external storage device, such as a hard disk, connected to or built in the server 100, and may include a storage medium, such as a detachable flash memory. Instead of providing the server 100 with the DB 115, the DB 115 may be provided in an external server or the like so that the server 100 can acquire the patient information, the medical professional information, the environment information, or the like from the external server by communication.

The server 100 may include an input device such as a keyboard or a mouse, and a display unit such as a liquid crystal display, for allowing a user to perform instructions or inputs.

[Patient Terminal]

Figure 3A:
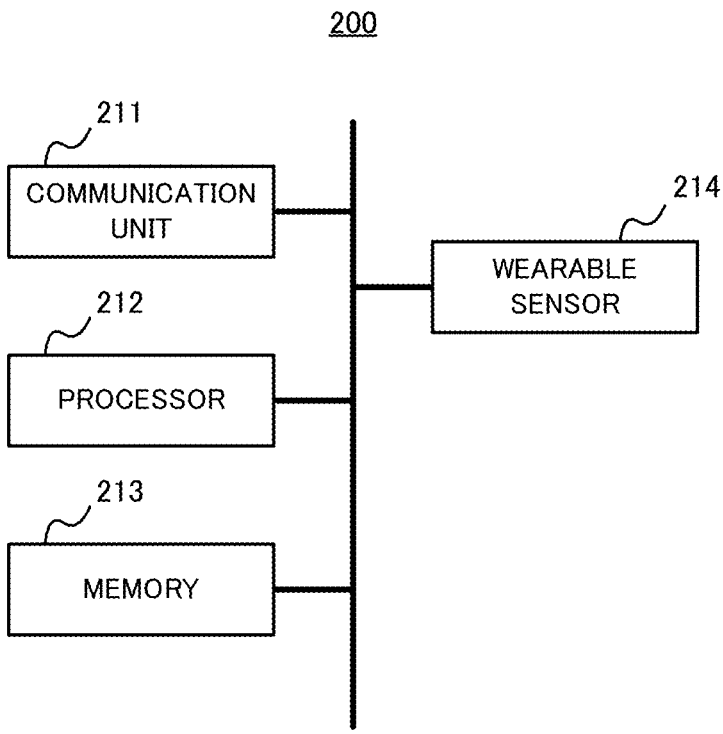
FIG. 3A is a block diagram showing a configuration of a patient terminal.

FIG. 3A is a block diagram showing a configuration of the patient terminal 200. The patient terminal 200 is, for example, a wristband type wearable device. The patient terminal 200 includes a communication unit 211, a processor 212, a memory 213, and a wearable sensor 214.

The communication unit 211 transmits and receives data to and from external devices. Specifically, the communication unit 211 transmits and receives information to and from the server 100. The communication unit 211 may communicate with beacons installed in the hospital by Bluetooth (registered trademark).

The processor 212 is a computer such as a CPU and controls the entire patient terminal 200 by executing a program prepared in advance. The processor 212 may be a GPU, a FPGA, a DSP, an ASIC, or the like.

The memory 213 may be a ROM and a RAM. The memory 213 stores various programs executed by the processor 212. The memory 213 is also used as a working memory during various processes performed by the processor 212.

The wearable sensor 214 includes a heart rate sensor, a temperature sensor, a perspiration sensor, and the like. The heart rate sensor measures a patient's heart rate. The temperature sensor measures a patient's body temperature. The perspiration sensor measures the perspiration amount of the patient. Note that the sensor is not limited to the above sensors, as long as it is a sensor capable of acquiring biomedical information of a patient.

The patient terminal 200 may include a GPS (Global Positioning System) receiver or the like to transmit the location information to the server 100.

[Medical Professional Terminal]

Figure 3B:
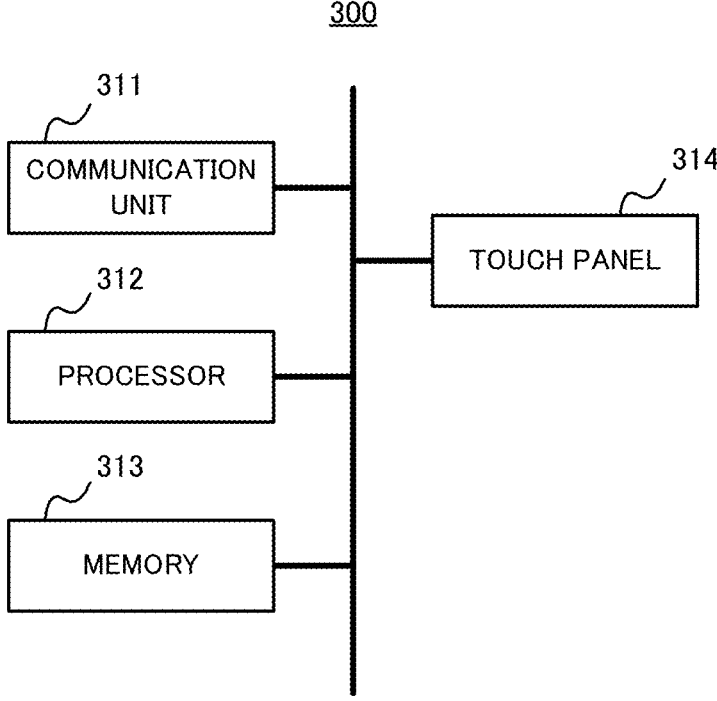
FIG. 3B is a block diagram showing a configuration of a medical professional terminal.

FIG. 3B is a block diagram showing a configuration of the medical professional terminal 300. The medical professional terminal 300 is, for example, a smartphone, a tablet terminal, or the like. The medical professional terminal 300 mainly includes a communication unit 311, a processor 312, a memory 313, and a touch panel 314. Incidentally, the administrator terminal 400 is also assumed to have the same configuration as the medical professional terminal 300.

The communication unit 311 transmits and receives data to and from the external devices. The communication unit 311 transmits and receives information to and from the server 100. The communication unit 311 may communicate with the beacons installed in the hospital by Bluetooth (registered trademark).

The processor 312 is a computer such as a CPU and controls the entire medical professional terminal 300 by executing a program prepared in advance. The processor 312 may be a GPU, a FPGA, a DSP, an ASIC, or the like.

The memory 313 may be a ROM and a RAM. The memory 313 is also used as a working memory during various processes performed by the processor 312.

The touch panel 314 displays information received by the medical professional terminal 300. The touch panel 314 also functions as an input device for a medical professional.

The medical professional terminal 300 may include a GPS receiver or the like to transmit the location information to the server 100.

[Function Configuration]

Figure 4:
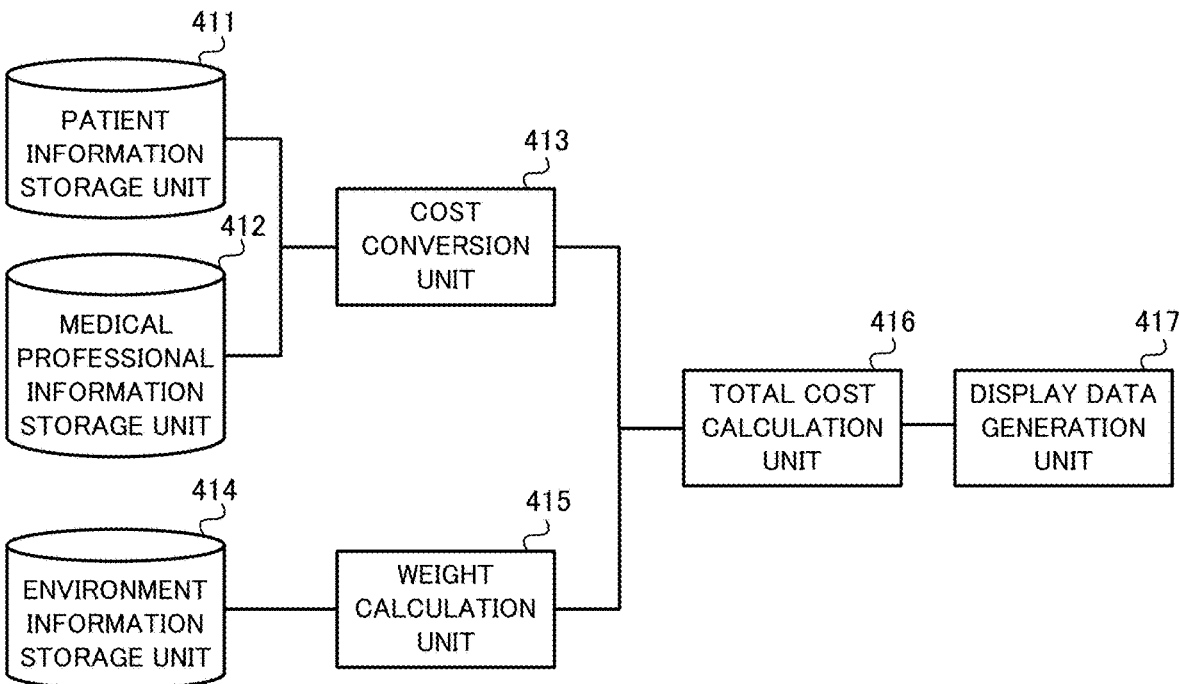
FIG. 4 is a block diagram showing a functional configuration of the server.

FIG. 4 is a block diagram showing a functional configuration of the server 100. The server 100 functionally includes a patient information storage unit 411, a medical professional information storage unit 412, a cost conversion unit 413, an environment information storage unit 414, a weight calculation unit 415, a total cost calculation unit 416, and a display data generation unit 417. The patient information storage unit 411, the medical professional information storage unit 412, and the environment information storage unit 414 are implemented by the DB 115 shown in FIG. 2. The cost conversion unit 413, the weight calculation unit 415, the total cost calculation unit 416, and the display data generation unit 417 are configured by the processor 112 shown in FIG. 2.

In the patient information storage unit 411, the patient information is stored. The server 100 updates the patient information each time the biomedical information of the patient is received from the patient terminal 200 or the thermographic camera installed in the hospital room.

FIG. 5 is an example of the data structure of the patient information. The patient information includes information such as a patient name, basic information of the patient, biomedical information, a disquiet score, and behavior of the patient. The basic information of the patient is information such as age and sex of the patients, and is registered when the patients are hospitalized or the like. The biomedical information is information such as a heart rate, a respiratory rate, blood pressure, a body temperature, a perspiration amount of the patient. The disquiet score is a score that indicates whether the patient is disquiet or non-disquiet. The disquiet score is, for example, a value equal to or larger than 0 and equal to or smaller than 1, and it is highly likely that the patient is disquiet when the value of disquiet score is close to 1. The server 100 determines the disquiet score based on pre-trained identification parameters and feature quantities regarding the biomedical information of the patients. The identification parameters are the parameters which associate the feature quantities of the biomedical information with the disquiet state or the non-disquiet state. The behavior of the patient is information such as whether or not there are movement in the patient. For example, the server 100 receives a video of the patient from the thermographic camera and determines whether or not the patient is moving, by using an image recognition model prepared in advance or the like.

In the medical professional information storage unit 412, the medical professional information is stored. FIG. 6 is an example of the data structure of the medical professional information. The medical professional information includes information such as a name of the medical professional, a length of service, a skill level, and patients in charge.

The cost conversion unit 413 acquires the patient information from the patient information storage unit 411. Then, the cost conversion unit 413 converts the patient information into costs.

First, the cost conversion unit 413 converts the information of each item included in the patient information, such as the biomedical information, the disquiet score, and the behavior of the patient, into a unified value based on a common criterion. For example, the cost conversion unit 413 uses a level as the common criterion, and sets the level higher as the patient's state becomes apart from the normal state. Specifically, when the patient's heart rate is within the range of the normal value, the cost conversion unit 413 sets the level to "0". On the other hand, when the patient's heart rate is outside the normal range, the cost conversion unit 413 sets the level higher than "0" based on the difference between the patient's heart rate and the normal value.

Next, the cost conversion unit 413 converts the patient information into the cost by referring to a predetermined cost conversion table or the like. For example, the cost conversion unit 413 converts the patient information into the cost by referring to the cost conversion table or the like associating a combination of levels of each item of the patient information with a cost for the combination. The method of converting the patient information into the cost is not limited to the method using the cost conversion table, and the cost conversion unit 413 may acquire the cost by adding the values of each item of the patient information that is unified based on a common criterion. The cost conversion unit 413 outputs the cost converted from the patient information (hereinafter, referred to as the "patient cost") to the total cost calculation unit 416.

The cost conversion unit 413 acquires the medical professional information from the medical professional information storage unit 412. In the same manner as described above, first, the cost conversion unit 413 converts the information of each item, such as the length of service, the skill level, and the patients in charge, which are included in the medical professional information, into a unified value based on a common criterion. Next, the cost conversion unit 413 converts the medical professional information into the cost by referring to a conversion table or the like that defines the relationship between the medical professional information and the costs in advance. The cost conversion unit 413 outputs the cost converted from the medical professional information (hereinafter, referred to as the "medical professional cost") to the total cost calculation unit 416.

In the environment information storage unit 414, the environment information is stored. FIG. 7 is an example of the data structure of the environment information. The environment information includes information such as a patient's name, patient's room information, and access information. The patient's room information is the type of room such as an ICU (Intensive Care Unit), a HCU (High Care Unit), and a general ward. The access information is information representing the proximity of the medical professional to the patients. In FIG. 7, distance information relating to the distance between the patient and the medical professional is used as the access information. The server 100 calculates the distance between the patient and the medical professional and updates the access information each time the location information is received from the patient terminal 200 and the medical professional terminal 300.

The weight calculation unit 415 acquires the environment information from the environment information storage unit 414. Then, the weight calculation unit 415 calculates weights based on the environment information. The weight calculation unit 415 calculates the weights from the environment information by referring to a weight conversion table that defines the relationship between the environment information and the weights. For example, the weight conversion table is set so that the weight becomes the largest when the type of room is the ICU, and the weight becomes smaller than the ICU when the type of room is the HCU or the general ward. In addition, the weight conversion table is set so that the closer the distance between the patient and the medical professional, the greater the weight. The weight calculation unit 415 may reduce the weight determined from the distance between the patient and the medical professional, when the location information of the patient terminal 200 and the medical professional terminal 300 cannot be accurately acquired due to a network failure or the like. The weight calculation unit 415 outputs the weights calculated from the type of room (hereinafter, also referred to as the "weight of the hospital room") and the weights calculated from the distance between the patient and the medical professional (hereinafter, also referred to as the "weight of the distance") to the total cost calculation unit 416.

The total cost calculation unit 416 acquires the patient cost and the medical professional cost from the cost conversion unit 413. The total cost calculation unit 416 acquires the weight of the hospital room and the weight of the distance from the weight calculation unit 415. The total cost calculation unit 416 calculates the total cost (ct) based on the patient cost (c1), the medical professional cost (c2), the weight of the hospital room (w1), and the weight of the distance (w2). Here, the total cost (ct) is calculated by one of the following equations, for example.

$$(ct)=(c1+c2)\times(w1+w2) \tag{1}$$

$$(ct)=(c1+c2)\times(w1\times w2) \tag{2}$$

$$(ct)=(c1\times w1)+(c2\times w2) \tag{3}$$

The total cost calculation unit 416 calculates the total costs and temporarily stores them in the memory 113. FIG. 8 is an example of the total costs. In FIG. 8, the total costs associated with the patients and the medical professional S and the total costs associated with the patients and the medical professional T are shown.

The total cost calculation unit 416 determines whether or not the patient needs to be treated based on the total cost of the patient. For example, the total cost calculation unit 416 determines that a patient whose total cost is equal to or larger than a predetermined threshold value is a patient who needs to be treated. Specifically, in FIG. 8, when the predetermined threshold value is "10", the total cost calculation unit 416 determines that the patient A, the patient C, and the patient E are the patients who need to be treated.

The total cost calculation unit 416 also determines which medical professional should treat which patient. For example, the total cost calculation unit 416 compares the total costs of the medical professionals for the patient who needs to be treated, and determines the medical professional who should treat the patient. Specifically, in FIG. 8, for patient A, the total cost of medical professional S is "14" and the total cost of medical professional T is "10". The total cost calculation unit 416 determines the medical professional S having the higher total cost as the medical professional who treats the patient A.

In addition, when the medical professional treats a plurality of patients, the total cost calculation unit 416 determines the order of treatment. The total cost calculation unit 416 assigns the order of treatment from the patient having the higher total cost. Specifically, in FIG. 8, when the medical professional S treats the patient A and the patient C, the total cost calculation unit 416 determines the order of treatment so that the patient C having the highest total cost is the first and the patient A having the next highest total cost is the second. The total cost calculation unit 416 outputs the patients who need to be treated, the medical professionals who treat, and the order of treatment to the display data generation unit 417.

The display data generation unit 417 acquires the patients who need to be treated, the medical professionals who treat, and the order of treatment from the total cost calculation unit 416. The display data generation unit 417 generates display data including the patients who need to be treated, the medical professionals who treat, and the order of treatment. At this time, the display data generation unit 417 generates the display data for the medical professionals and the display data for the administrator. The display data for the medical professionals are generated for each medical professional. The display data generation unit 417 transmits the generated display data to the medical professional terminals 300 and the administrator terminal 400.

In the above-described configuration, the cost conversion unit 413 is an example of an information acquisition means. The cost conversion unit 413, the weight calculation unit 415, and the total cost calculation unit 416 are examples of a treatment order determination means. The display data generation unit 417 is an example of an information output means.

[Display Example]

Next, a display example by the medical professional terminal 300 and the administrator terminal 400 will be described. FIG. 9A shows a display example of the medical professional terminal 300. FIG. 9A is a display example of the medical professional terminal 300 owned by the medical professional S. In this example, the patients who need to be treated, the total costs of the medical professional S for the patients, and the order of treatment of the patients who is treated by the medical professional S are displayed. Thus, with such a display, the medical professional S can understand that he or she should treat the patient C having the order of treatment of "1" first. The medical professional S can also understand that the medical professional T will treat the patient E and the patient F who are not treated by the medical professional S. FIG. 9B is a display example of the medical professional terminal 300 owned by the medical professional T. In this example, the patients who need to be treated, the total costs of the medical professional T for the patients, and the order of treatment of the patients who is treated by the medical professional T are displayed. Thus, with such a display, the medical professional T can understand that he or she should treat the patient E having the order of treatment of "1" first. In addition, the medical professional T can also understand that the medical professional S will treat the patient A and the patient C who are not treated by the medical professional T.

FIG. 10 is a display example of the administrator terminal 400. In this example, the patients who need to be treated, the total costs of each medical professional for the patients, the medical professionals who treat, and the order of treatment are displayed. Thus, with such a display, the administrator such as a doctor or a nurse chief can understand that which medical professional treat which patient.

[Determination Processing]

FIG. 11 is a flowchart of a treatment order determination processing according to the first example embodiment. This processing is realized by the processor 112 shown in FIG. 2, which executes a program prepared in advance and operates as each element shown in FIG. 4.

First, the cost conversion unit 413 acquires the patient information from the patient information storage unit 411 (step S11). The cost conversion unit 413 acquires the medical professional information from the medical professional information storage unit 412 (step S12). Then, the cost conversion unit 413 converts the patient information and the medical professional information into the costs, respectively (step S13). The cost conversion unit 413 converts the patient information and the medical professional information into the patient costs and the medical professional costs, respectively, by referring to the predetermined cost conversion tables or the like. Next, the weight calculation unit 415 acquires the environment information from the environment information storage unit 414 (step S14). Then, the weight calculation unit 415 calculates the weights based on the environment information (step S15). The weight calculation unit 415 calculates the weights from the environment information by referring to a predetermined weight conversion table or the like.

Next, the total cost calculation unit 416 acquires the patient costs and the medical professional costs from the cost conversion unit 413. The total cost calculation unit 416 acquires the weights from the weight calculation unit 415. Then, the total cost calculation unit 416 calculates the total costs based on the patient costs, the medical professional costs, and the weights (step S16). Then, the total cost calculation unit 416 compares the total costs with a predetermined threshold value (step S17), and the total cost calculation unit 416 determines that a patient whose total cost is equal to or larger than the predetermined threshold value is a patient who needs to be treated. Next, the total cost calculation unit 416 determines the medical professionals who treat and the order of treatment for the patients who need to be treated, and outputs those information to the display data generation unit 417. The display data generation unit 417 generates the display data including the patients who need to be treated, the medical professionals who treat, and the order of treatment. The display data generation unit 417 transmits the display data to the medical professional terminal 300 and the administrator terminal 400. The medical professional terminal 300 and the administrator terminal 400 display the received display data on the display (step S18). Then, the processing ends.

[Modification]

Next, a modification of the first example embodiment will be described. The following modification can be applied to the first example embodiment.

In the above example embodiment, as shown in FIG. 10, the patients who need to be treated, the medical professionals who treat, the order of treatment, or the like are displayed on the administrator terminal 400. However, the application of the present disclosure is not limited thereto. For example, as shown in FIG. 13, approval column of the administrator may be added to the display data. FIG. 13 shows a display example of the administrator terminal 400. In FIG. 13, the approval column is displayed in addition to the patients who need to be treated, the total costs of each medical professional for the patients, the medical professionals who treat, and the order of treatment. The administrator checks the display data received from the server 100, and taps the "OK" button when there is no problem in the contents of the display data. When the administrator taps the "OK" button, the server 100 generates display data including the approval of the administrator, and transmits the display data to the medical professional terminal 300. FIGS. 12A and 12B show display examples of the medical professional terminal 300. In FIGS. 12A and 12B, the column of approval results is displayed in addition to the patients who need to be treated, the total costs of each medical professional for the patients, the medical professionals who treat, and the order of treatment. Thus, the medical professional can confirm that the administrator gives permission to treat.

In addition, the administrator taps the "NG" button when there is a problem in the contents of the display data. At this time, the administrator may give an instruction to the medical professional individually or may correct the order of treatment and transmit the instruction to the server 100. The server 100 transmits display data reflecting the instruction contents of the administrator to the medical professional terminal 300.

Second Example Embodiment

FIG. 14 is a block diagram showing a functional configuration of an information processing device according to a second example embodiment. The information processing device 50 includes an information acquisition means 51, and a treatment order determination means 52.

FIG. 15 is a flowchart of processing in the second example embodiment. The information acquisition means 51 acquires patient information, medical professional information, and environment information (step S51). The treatment order determination means 52 determines an order of treatment of patients for each medical professional based on the patient information, the medical professional information, and the environment information (step S52).

According to the information processing device 50 of the second example embodiment, it is possible to efficiently treat patients.

A part or all of the example embodiments described above may also be described as the following supplementary notes, but not limited thereto.

(Supplementary Note 1)

An information processing device comprising:

an information acquisition means configured to acquire patient information, medical professional information, and environment information; and a treatment order determination means configured to determine an order of treatment of patients for each medical professional based on the patient information, the medical professional information, and the environment information.

(Supplementary Note 2)

The information processing device according to Supplementary note 1, further comprising an information output means configured to output the order of treatment of the patients to a terminal device of the medical professional.

(Supplementary Note 3)

The information processing device according to Supplementary note 1, wherein the environment information includes hospital room information.

(Supplementary Note 4)

The information processing device according to Supplementary note 1, wherein the environment information includes access information between the patients and the medical professionals.

(Supplementary Note 5)

The information processing device according to Supplementary note 1, wherein the treatment order determination means calculates costs based on the patient information and the medical professional information, calculates weights based on the environment information, and determines the order of treatment of the patients for each medical professional based on the costs and the weights.

(Supplementary Note 6)

The information processing device according to Supplementary note 2, wherein the information output means outputs the order of treatment of the patients for each medical professional.

(Supplementary Note 7)

The information processing device according to Supplementary note 6, wherein the information output means outputs the order of treatment of the patients who will be treated by another medical professional.

(Supplementary Note 8)

The information processing device according to Supplementary note 2, wherein the information output means outputs the order of treatment of the patients who will be treated by the medical professionals to a terminal device of an administrator.

(Supplementary Note 9)

An information processing method comprising:

acquiring patient information, medical professional information, and environment information; and determining an order of treatment of the patients for each medical professional based on the patient information, the medical professional information, and the environment information.

(Supplementary Note 10)

A recording medium recording a program which causes a computer to execute processing of:

acquiring patient information, medical professional information, and environment information; and determining an order of treatment of the patients for each medical professional based on the patient information, the medical professional information, and the environment information.

While the present disclosure has been described with reference to the example embodiments and examples, the present disclosure is not limited to the above example embodiments and examples. Various changes which can be understood by those skilled in the art within the scope of the present disclosure can be made in the configuration and details of the present disclosure.

This application is based upon and claims the benefit of priority from Japanese Patent Application 2022-121637, filed on Jul. 29, 2022, the disclosure of which is incorporated herein in its entirety by reference.

DESCRIPTION OF SYMBOLS

1 Patient's treatment order presentation system 1
100 Server
200 Patient terminal
300 Medical professional terminal
400 Administrator terminal
411 Patient information storage unit
412 Medical professional information storage unit 413 Cost conversion unit
414 Environment information storage unit
415 Weight calculation unit
416 Total cost calculation unit
417 Display data generation unit

The invention claimed is:

1. An information processing device comprising:
a memory configured to store instructions; and
one or more processors configured to execute the instructions to:
communicate data among a plurality of terminals of hospital staff in a hospital and sensors sensing biomedical information from each of a plurality of patients;
acquire, based on wirelessly communicating the data, patient information from each of the plurality of patients in the hospital, medical professional information, and environment information, and acquiring the patient information comprises obtaining the patient information from any of one or more thermographic cameras, installed in one or more hospital rooms in which the plurality of patients are located, and a plurality wristband devices each worn by ones of the plurality of patients, the patient information indicating locations of the ones of the plurality of patients, disquiet scores and behaviors of the plurality of patients and biomedical information indicating at least body temperatures of the ones of the plurality of patients, the sensors comprising the any of the one or more thermographic cameras and the plurality of wristband devices; and
determine and control one or more display devices to output of a display of disquiet of any of the patients and an order of treatment of the patients for each of medical professionals based on total costs associated with the patients and the medical professionals, the total costs being calculated from patient costs based on the patient information, medical professional costs based on the medical professional information, and weightings based on the environment information, the medical professionals being ones of the hospital staff, the medical professional information includes length of services and skill levels of the medical professionals, wherein
the environment information represents whether a network failure has been detected and any of patient names, types of rooms of the hospital, and proximities of each of the medical professionals to each of the plurality of patients, the types of the rooms of the hospital comprising an intensive care unit (ICU), a high care unit (HCU), and a general ward, and
the network failure represents a failure to convey data among any of the information processing device, the one or more thermographic cameras, the plurality of wristband devices, and terminals of the medical professionals.

2. The information processing device according to claim 1, wherein the one or more processors are further configured to output the order of treatment of the patients to a terminal device of at least one of the medical professionals, the terminal device comprising one of the display devices.

3. The information processing device according to claim 1, wherein the environment information includes hospital room information.

4. The information processing device according to claim 1, wherein the environment information includes access information between the patients and the medical professionals.

5. The information processing device according to claim 1, wherein the one or more processors calculate costs based on the patient information and the medical professional information, calculates weights based on the environment information, and determines the order of treatment of the patients for each of the medical professionals based on the costs and the weights.

6. The information processing device according to claim 2, wherein the one or more processors output the order of treatment of the patients for each of the medical professionals.

7. The information processing device according to claim 6, wherein the one or more processors output the order of treatment of the patients who will be treated by another medical professional.

8. The information processing device according to claim 2, wherein the one or more processors output the order of treatment of the patients who will be treated by the medical professionals to a terminal device of an administrator, the terminal device comprising one of the display devices.

9. An information processing method comprising:

communicating data among a plurality of terminals of hospital staff in a hospital and sensors sensing biomedical information from each of a plurality of patients;

acquiring, based on wirelessly communicating the data, patient information, medical professional information from each of the plurality of patients in the hospital, and environment information, and acquiring the patient information comprises obtaining the patient information from any of one or more thermographic cameras, installed in one or more hospital rooms in which the plurality of patients are located, and a plurality wristband devices each worn by ones of the plurality of patients, the patient information indicating locations of the ones of the plurality of patients, disquiet scores and behaviors of the plurality of patients and biomedical information indicating at least body temperatures of the ones of the plurality of patients, the sensors comprising the any of the one or more thermographic cameras and the plurality of wristband devices; and determining and controlling one or more display devices to output of a display of disquiet of any of the patients and an order of treatment of the patients for each of medical professionals based on total costs associated with the patients and the medical professionals, the total costs being calculated from patient costs based on the patient information, medical professional costs based on the medical professional information, and weightings based on the environment information, the medical professionals being ones of the hospital staff, the medical professional information includes length of services and skill levels of the medical professionals, wherein the environment information represents whether a network failure has been detected and any of patient names, types of rooms of the hospital, and proximities of each of the medical professionals to each of the plurality of patients, the types of the rooms of the hospital comprising an intensive care unit (ICU), a high care unit (HCU), and a general ward, and the network failure represents a failure to convey data among any of the information processing device, the one or more thermographic cameras, the plurality of wristband devices, and terminals of the medical professionals.

10. A non-transitory computer-readable recording medium recording a program which causes a computer to execute processing of:

communicating data among a plurality of terminals of hospital staff in a hospital and sensors sensing biomedical information from each of a plurality of patients;

acquiring, based on wirelessly communicating the data, patient information from each of the plurality of patients in the hospital, medical professional information, and environment information, and acquiring the patient information comprises obtaining the patient information from any of one or more thermographic cameras, installed in one or more hospital rooms in which the plurality of patients are located, and a plurality wristband devices each worn by ones of the plurality of patients, the patient information indicating locations of the ones of the plurality of patients, disquiet scores and behaviors of the plurality of patients and biomedical information indicating at least body temperatures of the ones of the plurality of patients, the sensors comprising the any of the one or more thermographic cameras and the plurality of wristband devices; and determining and controlling one or more display devices to output of a display of disquiet of any of the patients and an order of treatments of the patients for each of medical professionals based on total costs associated with the patients and the medical professionals, the total costs being calculated from patient costs based on the patient information, medical professional costs based on the medical professional information, and weightings based on the environment information, the medical professionals being ones of the hospital staff, the medical professional information includes length of services and skill levels of the medical professionals, wherein the environment information represents whether a network failure has been detected and any of patient names, types of rooms of the hospital, and proximities of each of the medical professionals to each of the plurality of patients, the types of the rooms of the hospital comprising an intensive care unit (ICU), a high care unit (HCU), and a general ward, and the network failure represents a failure to convey data among any of the information processing device, the one or more thermographic cameras, the plurality of wristband devices, and terminals of the medical professionals.

11. The information processing device according to claim 1, wherein the patient information is obtained at least from the plurality of wristband devices and further indicates any of heart rates, respiratory rates, blood pressures, and perspiration amounts of the ones of the plurality of patients.

12. The information processing device according to claim 11, wherein the patient information obtained from the plurality of wristband devices indicates each of heart rates, respiratory rates, blood pressures, and perspiration amounts of the ones of the plurality of patients.

13. The information processing device according to claim 12, wherein the environment information further represents each of patient names, the types of rooms of the hospital, and the proximities of each of the medical professionals to each of the plurality of patients.

\*    \*    \*    \*    \*